United States Patent
Kim et al.

(10) Patent No.: US 11,715,454 B2
(45) Date of Patent: Aug. 1, 2023

(54) BEAMFORMING DEVICE, METHOD OF CONTROLLING THE SAME, AND ULTRASOUND DIAGNOSTIC APPARATUS

(71) Applicants: SAMSUNG MEDISON CO., LTD., Gangwon-do (KR); INDUSTRY-UNIVERSITY COOPERATION FOUNDATION SOGANG UNIVERSITY, Seoul (KR)

(72) Inventors: Kang Sik Kim, Suwon-si (KR); Tai-Kyong Song, Seoul (KR); Sung Ho Kim, Gangwon-do (KR); Sua Bae, Seoul (KR); Hyun Woo Song, Seoul (KR); Jin Tae Jang, Seoul (KR)

(73) Assignees: SAMSUNG MEDISON CO. LTD., Gangwon-Do (KR); INDUSTRY-UNIVERSITY COOPERATION FOUNDATION SOGANG UNIVERSITY, Seoul (KR)

( * ) Notice: Subject to any disclaimer, the term of this patent is extended or adjusted under 35 U.S.C. 154(b) by 0 days.

(21) Appl. No.: 17/265,971

(22) PCT Filed: Jul. 17, 2019

(86) PCT No.: PCT/KR2019/008803
§ 371 (c)(1),
(2) Date: Feb. 4, 2021

(87) PCT Pub. No.: WO2020/036321
PCT Pub. Date: Feb. 20, 2020

(65) Prior Publication Data
US 2021/0295816 A1    Sep. 23, 2021

(30) Foreign Application Priority Data
Aug. 16, 2018 (KR) .................. 10-2018-0095573

(51) Int. Cl.
*G10K 11/34* (2006.01)
*A61B 8/00* (2006.01)
(Continued)

(52) U.S. Cl.
CPC .......... *G10K 11/346* (2013.01); *A61B 8/4488* (2013.01); *A61B 8/461* (2013.01);
(Continued)

(58) Field of Classification Search
None
See application file for complete search history.

(56) References Cited

U.S. PATENT DOCUMENTS 5,570,691 A * 11/1996 Wright ................. G10K 11/346
600/447
6,898,235 B1 * 5/2005 Carlin .................... H04B 1/001
342/147
(Continued)

FOREIGN PATENT DOCUMENTS

EP   1952175 A2   8/2008
KR   10-1509447 B1   4/2015
(Continued)

OTHER PUBLICATIONS

Cordeiro, Rui Fiel. Digital Beam-steering in a Parametric Array. Diss. MS thesis, Universidade de Aveiro, Portugal, 2012. (Year: 2012).*
(Continued)

*Primary Examiner* — Isam A Alsomiri
*Assistant Examiner* — Jonathan D Armstrong
(74) *Attorney, Agent, or Firm* — Morgan, Lewis & Bockius LLP

(57) ABSTRACT

A beamforming device includes a sampler configured to sample a signal reflected from a focal point and received to a transducer array; a mixer configured to separate the
(Continued)

sampled signal into an in-phase component signal and a quadrature component signal; a low pass filter configured to perform filtering on the in-phase component signal and the quadrature component signal; a decimator configured to perform decimation on the filtered in-phase component signal and quadrature component signal; a sampling delay compensator configured to compensate a sampling time delay based on a preset time delay resolution for the decimated in-phase component signal and quadrature component signal; a phase rotator configured to compensate a phase delay based on a preset phase resolution for the in-phase component signal and the quadrature component signal for which the sampling time delay is compensated; and a delay calculator configured to calculate a time delay resolution and the phase resolution, and to apply each to the sampling delay compensator and the phase rotator.

14 Claims, 15 Drawing Sheets

(51) Int. Cl.
*G01S 7/52* (2006.01)
*A61B 8/08* (2006.01)
*G01S 15/89* (2006.01)

(52) U.S. Cl.
CPC .......... *A61B 8/5207* (2013.01); *G01S 7/5202* (2013.01); *G01S 7/52025* (2013.01); *G01S 7/52046* (2013.01); *G01S 15/8915* (2013.01)

(56) References Cited

U.S. PATENT DOCUMENTS

| | | | | |
|---|---|---|---|---|
| 7,202,941 | B2* | 4/2007 | Munro | G01S 17/10 |
| | | | | 356/5.1 |
| 10,324,169 | B2* | 6/2019 | Tua | G01S 7/4008 |
| 10,353,062 | B2* | 7/2019 | Warke | G01S 7/4052 |
| 10,772,609 | B2* | 9/2020 | Chen | A61B 8/5207 |
| 2004/0135992 | A1* | 7/2004 | Munro | G01S 17/10 |
| | | | | 356/4.01 |
| 2006/0074320 | A1 | 4/2006 | Yoo et al. | |
| 2007/0229336 | A1 | 10/2007 | Liu et al. | |
| 2008/0007709 | A1* | 1/2008 | Bamji | G01C 25/00 |
| | | | | 356/5.01 |
| 2016/0228092 | A1* | 8/2016 | Kim | G01S 7/5208 |
| 2017/0184716 | A1 | 6/2017 | Bini | |
| 2020/0259540 | A1* | 8/2020 | Walling | H03K 3/0315 |

FOREIGN PATENT DOCUMENTS

| | | |
|---|---|---|
| KR | 10-2016-0070603 A | 6/2016 |
| KR | 10-2016-0097862 A | 8/2016 |
| WO | 2007/056104 A2 | 5/2007 |

OTHER PUBLICATIONS

International Written Opinion and Search Report dated Nov. 19, 2019 issued in International Patent Application No. PCT/KR2019/008803 (partial English translation).
European Search Report dated May 6, 2022 issued in European Patent Application No. 19849814.9.

* cited by examiner

● : INTERPOLATED SAMPLES

FIG.12

Ex)
If Q = 4 bits (M = $2^4$), $d_\lambda$ = 101011.00110111
→ address = 0011

$d_\lambda$ = 101011.01101111
→ address = 0111

360

| add | LUT | |
|---|---|---|
| 0000 | $\cos(2\pi(0/16))$ | $\sin(2\pi(0/16))$ |
| 0001 | $\cos(2\pi(1/16))$ | $\sin(2\pi(1/16))$ |
| 0010 | $\cos(2\pi(2/16))$ | $\sin(2\pi(2/16))$ |
| 0011 | $\cos(2\pi(3/16))$ | $\sin(2\pi(3/16))$ |
| ⋮ | | |
| 0111 | $\cos(2\pi(7/16))$ | $\sin(2\pi(7/16))$ |
| ⋮ | | |
| 1111 | $\cos(2\pi(15/16))$ | $\sin(2\pi(15/16))$ |
| | ↑ | ↑ |
| | $\cos(2\pi(m/M))$ | $\sin(2\pi(m/M))$ |

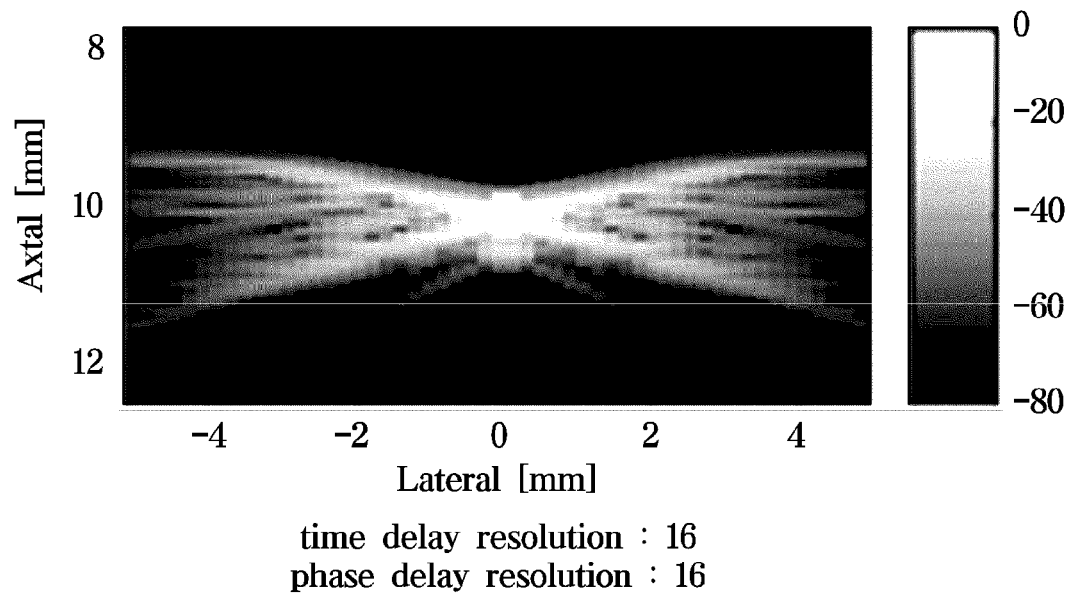

time delay resolution : 16
phase delay resolution : 128

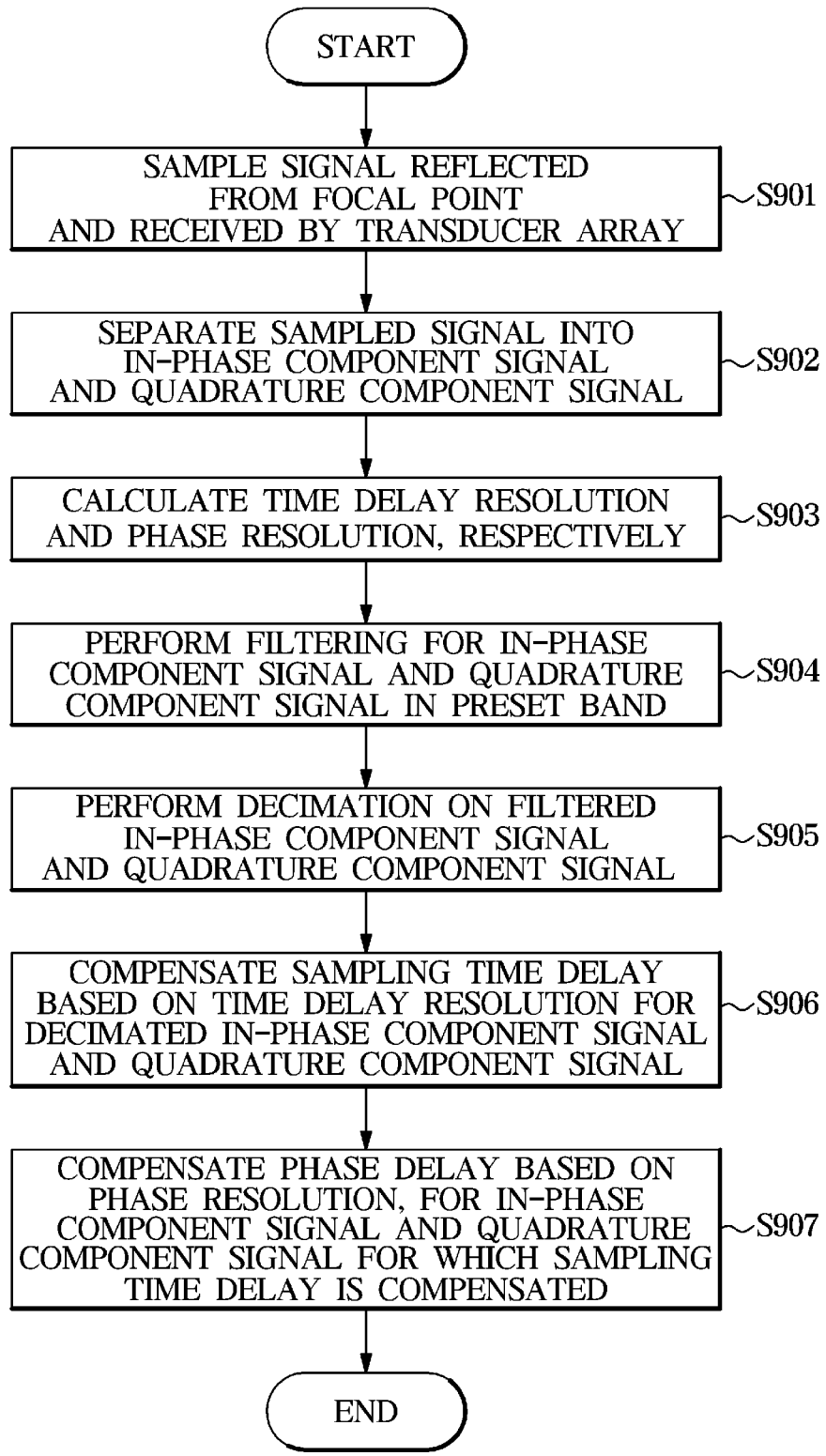

BEAMFORMING DEVICE, METHOD OF CONTROLLING THE SAME, AND ULTRASOUND DIAGNOSTIC APPARATUS

CROSS-REFERENCE OF RELATED APPLICATIONS

This application is the U.S. National Phase under 35 U.S.C. § 371 of International Patent Application No. PCT/KR2019/008803, filed on Jul. 17, 2019, which in turn claims the benefit of Korean Application No. 10-2018-0095573, filed on Aug. 16, 2018, the entire disclosures of which applications are incorporated by reference herein.

TECHNICAL FIELD

The present disclosure relates to a beamforming device, a method of controlling the same, and an ultrasound diagnostic apparatus.

BACKGROUND ART

Ultrasound diagnostic apparatuses operate to irradiate an ultrasound signal generated from an ultrasound probe transducer to a target site inside an object through the surface of the object and noninvasively acquire tomographic images or blood stream images of soft tissues using information about an ultrasound signal (an ultrasound echo signal) reflected from the object.

The ultrasound diagnostic apparatus has advantages in that it is compact and inexpensive, is displayable in real time, and has high safety compared to X-ray diagnostic devices due to having no risk of exposure to X-rays or the like, and thus are widely used for cardiac, breast, abdominal, urinary, and obstetrical diagnoses.

DISCLOSURE

Technical Problem

An aspect of the present disclosure is to provide a beamforming device capable of independently compensating for a time delay and a phase delay by independently applying a time delay resolution and a phase resolution, a method of controlling the same, and an ultrasound diagnostic apparatus.

Another aspect of the present disclosure is to provide a beamforming device capable of reducing an amount of computation for phase rotation without increasing hardware complexity by using a lookup table when performing phase rotation for phase delay compensation, a method of controlling the same, and an ultrasound diagnostic apparatus.

Another aspect of the present disclosure is to provide a beamforming device capable of improving beamforming performance by performing phase rotation with a sufficiently large number of phase quantization levels while reducing hardware complexity by applying the phase resolution higher than the time delay resolution, a method of controlling the same, and an ultrasound diagnostic apparatus.

Technical Solution

An aspect of the disclosure provides a beamforming device including: a sampler configured to sample a signal reflected from a focal point and received to a transducer array; a mixer configured to separate the sampled signal into an in-phase component signal and a quadrature component signal; a low pass filter configured to perform filtering on the in-phase component signal and the quadrature component signal; a decimator configured to perform decimation on the filtered in-phase component signal and quadrature component signal; a sampling delay compensator configured to compensate a sampling time delay based on a preset time delay resolution for the decimated in-phase component signal and quadrature component signal; a phase rotator configured to compensate a phase delay based on a preset phase resolution for the in-phase component signal and the quadrature component signal for which the sampling time delay is compensated; and a delay calculator configured to calculate a time delay resolution and the phase resolution, and to apply each to the sampling delay compensator and the phase rotator.

The phase rotator may include a look up table configured to store a phase delay compensation value corresponding to the phase resolution, and may be configured to compensate the phase delay by referring to the lookup table.

The phase rotator may be configured to calculate the phase delay compensation value using a preset relationship between a distance from the focal point to an element of the transducer array and an ultrasound wavelength and the phase resolution, and to store the calculated phase delay compensation value in the lookup table.

The phase rotator may be configured to calculate an address of the lookup table to be referred using a preset relationship between a distance from the focal point to an element of the transducer array and an ultrasound wavelength and the phase resolution.

The delay calculator may be configured to calculate the time delay resolution and the phase resolution as different values using an error model defined based on an average of an amplitude error and an average of a phase error.

The low pass filter may include an interpolation filter configured to increase an amount of data of the in-phase component signal and the quadrature component signal according to the time delay resolution.

Another aspect of the disclosure provides a method of controlling a beamforming device including: sampling, by a sampler, a signal reflected from a focal point and received to a transducer array; separating, by a mixer, the sampled signal into an in-phase component signal and a quadrature component signal; calculating, by a delay calculator, a time delay resolution and a phase resolution; filtering, by a low pass filter, the in-phase component signal and the quadrature component signal in a preset band; performing, by a decimator, decimation on the filtered in-phase component signal and quadrature component signal; compensating, by a sampling delay compensator, a sampling time delay based on a preset time delay resolution for the decimated in-phase component signal and quadrature component signal; and compensating, by a phase rotator, a phase delay based on the phase resolution for the in-phase component signal and the quadrature component signal for which the sampling time delay is compensated.

The compensating of the phase delay may include compensating the phase delay by referring to a look up table stored a phase delay compensation value corresponding to the phase resolution.

The compensating of the phase delay may further include calculating the phase delay compensation value using a preset relationship between a distance from the focal point to an element of the transducer array and an ultrasound wavelength and the phase resolution; and storing the calculated phase delay compensation value in the lookup table.

The compensating of the phase delay may further include calculating an address of the lookup table to be referred using a preset relationship between a distance from the focal point to an element of the transducer array and an ultrasound wavelength and the phase resolution.

The calculating of the time delay resolution and the phase resolution may include calculating the time delay resolution and the phase resolution as different values using an error model defined based on an average of an amplitude error and an average of a phase error.

The filtering may further include performing an interpolation to increase an amount of data of the in-phase component signal and the quadrature component signal according to the time delay resolution.

Another aspect of the disclosure provides an ultrasound diagnostic apparatus including: a probe including a transducer array configured to transmit and receive ultrasound signals, and a beamforming device; and a main body configured to process the signal received from the probe to generate an ultrasound image, and to display the generated ultrasound image. The beamforming device may be configured to sample the signal reflected from a focal point and received to the transducer array, to separate the sampled signal into an in-phase component signal and a quadrature component signal, to calculate a time delay resolution and a phase resolution, and to compensate a sampling time delay and a phase delay based on the time delay resolution and the phase resolution for the in-phase component signal and the quadrature component signal.

The beamforming device may include a look up table configured to store a phase delay compensation value corresponding to the phase resolution, and may be configured to compensate the phase delay by referring to the lookup table.

The beamforming device may be configured to calculate the phase delay compensation value using a preset relationship between a distance from the focal point to an element of the transducer array and an ultrasound wavelength and the phase resolution, and to store the calculated phase delay compensation value in the lookup table.

The beamforming device may be configured to calculate an address of the lookup table to be referred using a preset relationship between a distance from the focal point to an element of the transducer array and an ultrasound wavelength and the phase resolution.

The beamforming device may be configured to calculate the time delay resolution and the phase resolution as different values using an error model defined based on an average of an amplitude error and an average of a phase error.

Advantageous Effects

According to a beamforming device, a method of controlling the beamforming device, and an ultrasound diagnostic apparatus of the disclosure, a time delay and a phase delay may be independently compensated by independently applying a time delay resolution and a phase resolution, a method of controlling the same, and an ultrasound diagnostic apparatus.

In addition, by using a lookup table when performing phase rotation for phase delay compensation, it is possible to reduce an amount of computation for phase rotation without increasing hardware complexity.

In addition, by applying the phase resolution higher than the time delay resolution, it is possible to improve beamforming performance by performing phase rotation with a sufficiently large number of phase quantization levels while reducing the hardware complexity.

DESCRIPTION OF DRAWINGS

FIGS. 11 and 12 are views for describing a method of configuring a lookup table.

FIG. 14 is a flowchart of a beamforming method according to an embodiment.

MODES OF THE INVENTION

Figure 1:
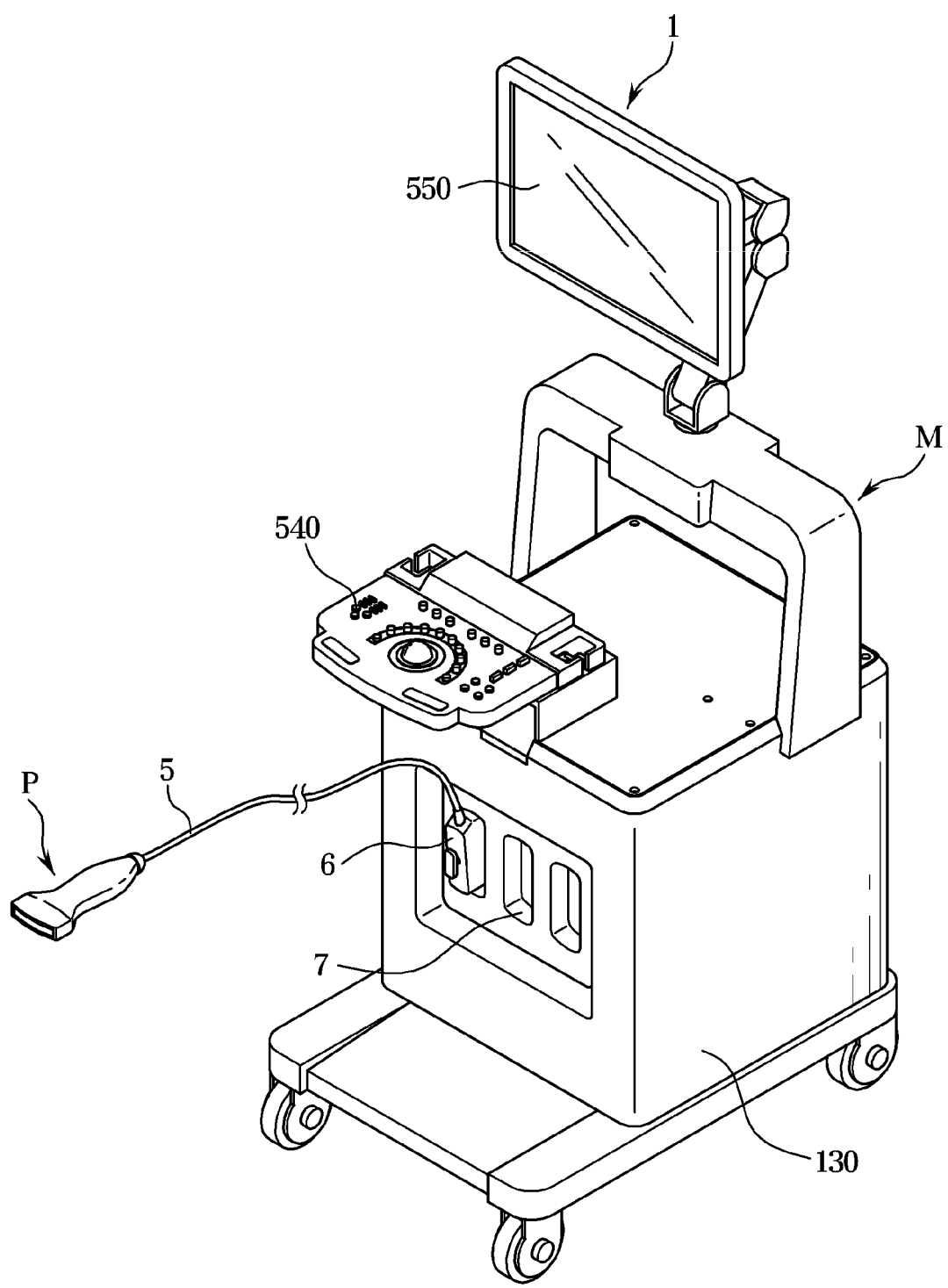
FIG. 1 is a view illustrating an exterior of an ultrasound diagnostic apparatus according to an embodiment.

Reference will now be made in detail to embodiments, examples of which are illustrated in the accompanying drawings.

Like reference numerals refer to like elements throughout the specification. Not all elements of the embodiments of the disclosure will be described, and the description of what are commonly known in the art or what overlap each other in the exemplary embodiments will be omitted. The terms as used throughout the specification, such as "~part," "~module," "~member," "~block," etc., may be implemented in software and/or hardware, and a plurality of "~parts," "~modules," "~members," or "~blocks" may be implemented in a single element, or a single "~part," "~module," "~member," or "~block" may include a plurality of elements.

It will be further understood that the term "connect" and its derivatives refer both to direct and indirect connection, and the indirect connection includes a connection over a wireless communication network.

The terms "include (or including)" and "comprise (or comprising)" are inclusive or open-ended and do not exclude additional, unrecited elements or method steps, unless otherwise mentioned. It will be further understood that the term "member" and its derivatives refer both to when a member is in contact with another member and when another member exists between the two members.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section.

It is to be understood that the singular forms "a," "an," and "the" include plural references unless the context clearly dictates otherwise.

Reference numerals used for method steps are merely used for convenience of explanation, but not to limit an order of the steps. Thus, unless the context clearly dictates otherwise, the written order may be practiced otherwise.

Hereinafter, operation principles and embodiments of the disclosure will be described with reference to accompanying drawings.

FIG. 1 is a view illustrating an exterior of an ultrasound diagnostic apparatus according to an embodiment.

Referring to FIG. 1, an ultrasound diagnostic apparatus 1 may include an ultrasound probe P that transmits ultrasounds to an object, receives ultrasound signals from the object and converts ultrasound echo signals to an electric signal, and a main body M connected to the ultrasound probe P and equipped with an input 540 and a display 550 for displaying ultrasound images.

The ultrasound probe P may be connected to the main body M of the ultrasound diagnostic apparatus 1 via a cable 5, for receiving various signals required to control the ultrasound probe P or forwarding analog or digital signals that correspond to the ultrasound echo signals received by the ultrasound probe P to the main body M. However, embodiments of the ultrasound probe P are not limited thereto, and may be implemented with a wireless probe to exchange signals with the main body M over a network formed between the ultrasound probe P and the main body M.

One end of the cable 5 may be connected to the ultrasound probe P, and the other end of the cable 5 may be connected to a connector 6 that may be coupled to or decoupled from a slot 7 of the main body M. The main body M and the ultrasound probe P may exchange control commands or data via the cable 5. For example, when the user inputs information about a focal depth, an aperture size or shape, a steering angle or the like through the input 540, the information may be transmitted to the ultrasound probe P via the cable 5 and used by a beamforming device 100.

Alternatively, in the case that the ultrasound probe P is implemented with a wireless probe as mentioned above, the ultrasound probe P is connected to the main body M not through the cable 5 but through a wireless network. Even in the case that the ultrasound probe P is connected to the main body M over a wireless network, control commands or data may be exchanged between the main body M and the ultrasound probe P.

Figure 2:
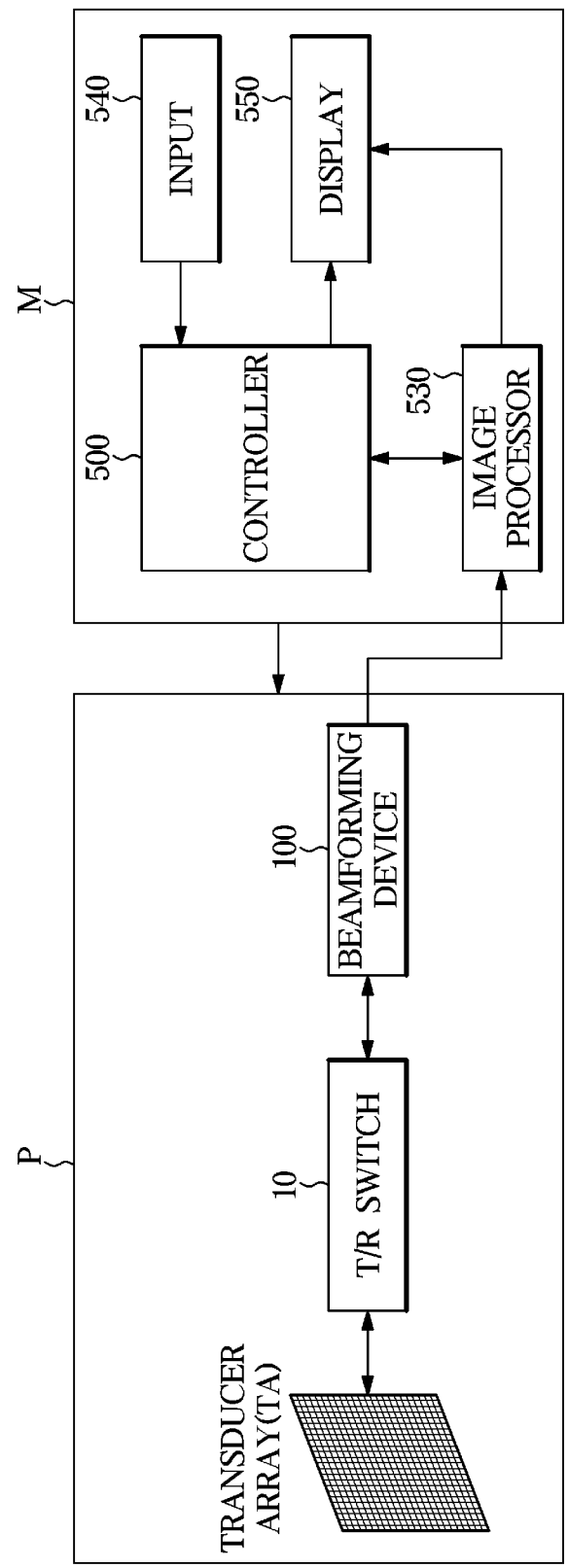
FIG. 2 is a control block diagram of an ultrasound diagnostic apparatus according to an embodiment.

FIG. 2 is a control block diagram of an ultrasound diagnostic apparatus according to an embodiment.

Referring to FIG. 2, the ultrasound probe P may include an ultrasound transducer array TA, a transmission/reception (T/R) switch 10 and a beamforming device 100. The main body M may include a controller 500, an image processor 530, the input 540, and the display 550.

Looking at a configuration of the main body M, the controller 500 may control overall operation of the ultrasound diagnostic apparatus 1. Particularly, the controller 500 may control the T/R switch 10, the beamforming device 100, the image processor 530, the display 550, and the like.

The controller 500 may calculate a delay profile for a plurality of ultrasound transducer elements e that constitute the ultrasound transducer array TA, and calculate time delay values depending on differences in distance between the plurality of ultrasound transducer elements e and a focal point of the object based on the calculated delay profile. This operation may be performed in the beamforming device 100 of the ultrasound probe P.

The image processor 530 may generate an ultrasound image of a target site inside the object based on ultrasound signals focused by the beamforming device 100. Particularly, the image processor 530 may create a coherent two dimensional (2D) or 3D image of the target site inside the object based on the focused ultrasound signals.

The image processor 530 may also convert the coherent image information to ultrasound image information for a diagnostic mode, such as a brightness mode (B-mode), a doppler mode (D-mode), etc. For example, when the diagnostic mode is set to the B-mode, the image processor 530 may perform e.g., an analog-to-digital (A/D) conversion process and compose ultrasound image information in real time for an image of the B-mode.

When a scan mode is set to the D-mode, the image processor 530 may extract phase-change information from the ultrasound signal, calculate information about e.g., blood flow at each point in the scanned cross-section, such as speed, power, or dispersion, and compose ultrasound image information in real time for the D-mode image.

The input 540 may receive an instruction or command from a user, and the controller 500 may control the ultrasound diagnostic apparatus 1 according to the command input by the user. The user may input or set a command to start diagnosis, a command to select the diagnostic mode, such as an amplitude mode (A-mode), the B-mode, a color mode (C-mode), the D-mode, and a motion mode (M-mode), region of interest (ROI) setting information including a size and a location of the ROI, etc., through the input 540.

The input 540 may include various means for the user to input data, instructions, or commands, such as a keyboard, a mouse, a trackball, a tablet, a touch screen module, etc.

The display 550 may display menus or instructions required in ultrasound diagnosis, and the ultrasound image obtained in the process of the ultrasound diagnosis. The display 550 may display the ultrasound image of the target site inside the object, which is created by the image processor 530. The ultrasound image to be displayed in the display 550 may be an ultrasound image in the A-mode or B-mode, or may be a 3D ultrasound image. The display 550 may be implemented in various display schemes known to the public, such as Cathode Ray Tube (CRT), Liquid Crystal Display (LCD), etc.

The ultrasound diagnostic apparatus 1 may include other components in addition to what are described above, without being limited thereto.

Looking at a configuration of the ultrasound probe P, the ultrasound transducer array TA is arranged at an end of the ultrasound probe P. The ultrasound transducer array TA refers to an array of a plurality of ultrasound transducer elements e.

The ultrasound transducer array TA may generate ultrasound while vibrating due to a pulse signal or alternate current (AC) applied thereto. The ultrasound is transmitted to the target site inside the object. In this case, the ultrasound generated by the ultrasound transducer array TA may be focused and transmitted to multiple target sites inside the object. That is, the ultrasound may be multi-focused and transmitted to the multiple target sites.

The ultrasound generated by the ultrasound transducer array TA may reflect off the target site inside the object and may return to the ultrasound transducer array TA. The ultrasound transducer array TA may then receive an echo ultrasound reflecting and returning from the target site. When the echo ultrasound arrives at the ultrasound transducer array TA, the ultrasound transducer array TA may oscillate at a certain frequency corresponding to a frequency of the echo ultrasound and output alternate current of a frequency corresponding to the oscillation frequency. Accordingly, the ultrasound transducer array TA may convert the received echo ultrasound to a certain electric signal.

Since each element e receives the echo ultrasound and outputs the electric signal, the ultrasound transducer array TA may output electric signals on multiple channels. The number of the channels may be the same as the number of ultrasound transducer elements e that constitute the ultrasound transducer array TA.

The ultrasound transducer elements e may include piezoelectric oscillators or thin films. When alternate current is applied to the piezoelectric oscillators or thin films from a power source, the piezoelectric oscillators or thin films oscillate at a certain frequency due to the applied alternate current and generate ultrasound with the certain frequency. On the other hand, the piezoelectric oscillators or thin films oscillate at a certain frequency of the echo ultrasound when the echo ultrasound arrives at the piezoelectric oscillators or thin films, and output alternate current of a frequency corresponding to the oscillation frequency.

For the ultrasound transducers, e.g., magnetostrictive ultrasound transducers that use magnetostrictive effect of a magnetic substance, piezoelectric ultrasound transducers that use piezoelectric effect of a piezoelectric substance, or capacitive Micromachined Ultrasound Transducers (cMUTs) that transmit and receive ultrasounds by means of oscillation of hundreds or thousands of micromachined thin films may be used. In addition, other types of transducer that may generate ultrasound from an electrical signal or generate an electrical signal from ultrasound may also be an example of the aforementioned ultrasound transducer.

The beamforming device 100 may apply transmit pulses for the transducer array TA to transmit the ultrasound signal to the target site inside the object. The beamforming device 100 may also perform a certain process and reception beamforming on the ultrasound echo signal received from the transducer array TA. Further, the beamforming device 100 may be included in the main body M to perform beamforming.

Particularly, in obtaining an image using the ultrasound signal, a beamforming technique is applied to increase a resolution of the image. The beamforming may include a transmission beamforming that simultaneously focuses on one focal point by giving an appropriate time delay to the ultrasound signal transmitted from the plurality of transducer elements, and a reception beamforming in which a time delay is applied to the ultrasound echo signal reflected from the focal point and returned to the transducer element and summed at the same time.

In general, a baseband based I/Q (In-phase/Quadrature) beamformer may apply the time delay using a sampled value during the beamforming. In addition, the I/Q beamformer may include a phase rotator to compensate for phase delay. At this time, there may be a time delay error (or amplitude error) caused by sampling and a phase delay error occurring according to a phase quantization level. That is, in order to restore the ultrasound echo signal reflected from the focal point (image point), the time delay and the phase delay must be compensated.

In this regard, a prior art compensates by calculating the phase delay as an ideal value rather than a quantized value, or compensates for the phase delay by applying a time delay resolution and the phase quantization level corresponding to an interpolation factor of a sampling frequency and the phase delay corresponding to the phase quantization level at the same level.

However, when the phase delay is calculated and compensated by the ideal value, there is a problem that the resources required to calculate the phase delay increase, and hardware complexity increases accordingly. And there is a problem that applying the time delay resolution and the phase resolution at the same level is possible only when the phase resolution is less than the number of channels. The disclosure aims to solve this problem.

A series of processing and beamforming performed by the beamforming device 100 will be described in detail with reference to FIGS. 3 to 5 below.

Figure 3:
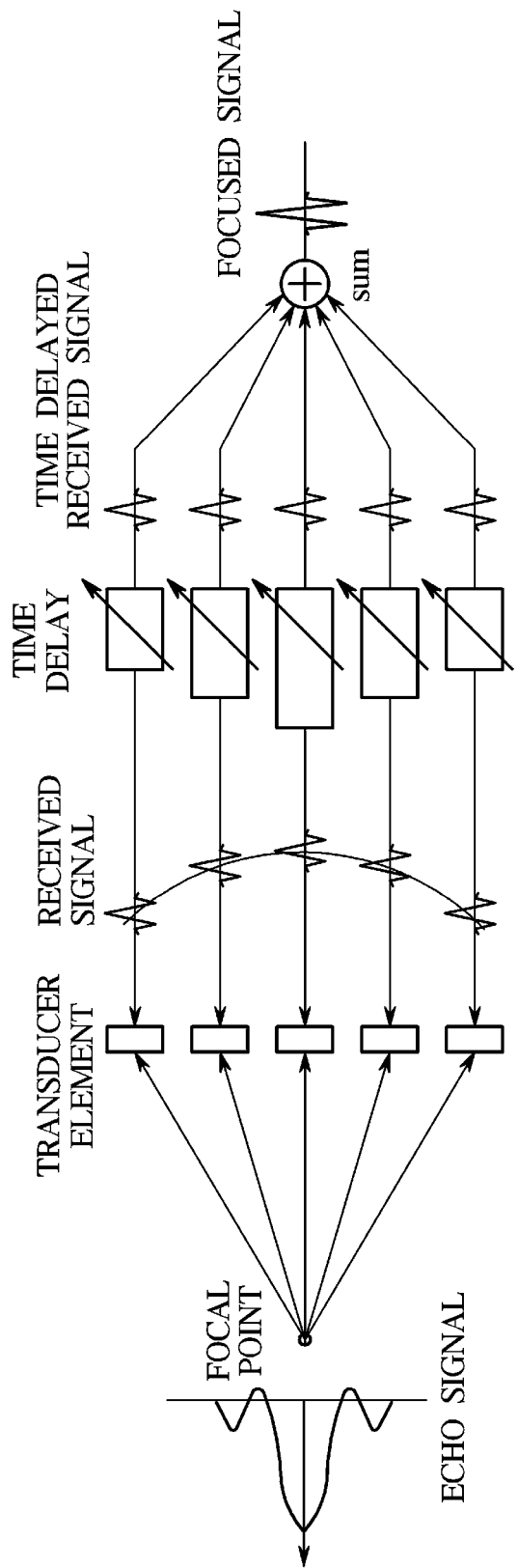
FIG. 3 is a view illustrating a time delay of a received signal applied during reception beamforming.

FIG. 3 is a view illustrating a time delay of a received signal applied during reception beamforming.

When the ultrasound signals in the same phase arrive at the focal point by performing the transmission beamforming, the ultrasound echo signals are generated at the focal point and return to the transducer array TA.

Distances from the respective transducer elements e to the focal point are different when the echo ultrasound is received from the focal point, so the ultrasound echo signals arrive at the respective transducer elements e at different points of time. Particularly, the ultrasound echo signal arrives first at an element nearest to the focal point, and arrives last at an element farthest from the focal point.

Since the magnitude of the ultrasound echo signal is very small, a single ultrasound echo signal received by each element (e) is not enough to obtain necessary information. Therefore, the reception beamforming sums appropriate delay times to received signals arriving at each element at the same time, thereby improving the signal to noise ratio (SNR).

Figure 4:
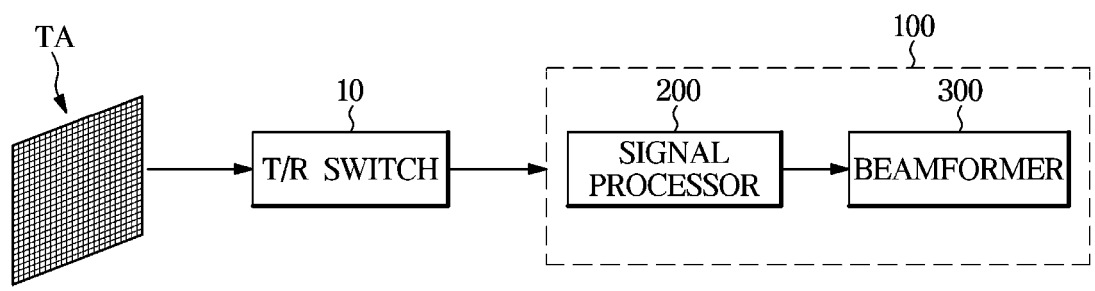
FIG. 4 is a control block diagram of a beamforming device according to an embodiment.

FIG. 4 is a control block diagram of a beamforming device according to an embodiment.

Referring to FIG. 4, the beamforming apparatus 100 may include a signal processor 200 and a beamformer 300. An electric signal converted by the transducer array TA may be input to the signal processor 200. The signal processor 200 may amplify the electric signal converted from the echo ultrasound signal prior to performing a signal process or time-delay process, and adjust the gain or compensate for attenuation from the depth.

The signal processor 200 may include a low noise amplifier (LNA) for reducing noise of the electric signal input from the ultrasound transducer array TA, and a variable gain amplifier (VGA) for adjusting a gain value based on the input signal. The VGA may correspond to a time gain compensation (TGC) amplifier that compensates for a gain based on a distance to the focal point, without being limited thereto. In addition, the signal processor 200 may be disposed behind the beamformer 300.

The beamformer 300 may perform the aforementioned beamforming on the electric signal received from the signal processor 200. The beamformer 300 may perform signal intensification through superposition of the electric signals received from the signal processor 200.

The signal beamformed by the beamformer 300 is converted to a digital signal by the AD converter, which is sent to the image processor 530 of the main body M. With the AD converter equipped in the main body M, an analog signal beamformed by the beamformer 300 may be sent to the main body M and then converted to a digital signal in the main body M. Alternatively, the beamformer 300 may be a digital beamformer.

The digital beamformer may include a storage for storing sampled analog signals, a sampling cycle controller for controlling a sampling cycle, an amplifier for adjusting the magnitude of the sample, an anti-aliasing low pass filter for preventing aliasing prior to sampling, a bandpass filter for selectively passing a desired frequency band, an interpolation filter for increasing a sampling rate when beamforming is performed, and a high pass filter for filtering out a direct current (DC) component or signals of a low frequency band.

Figure 5:
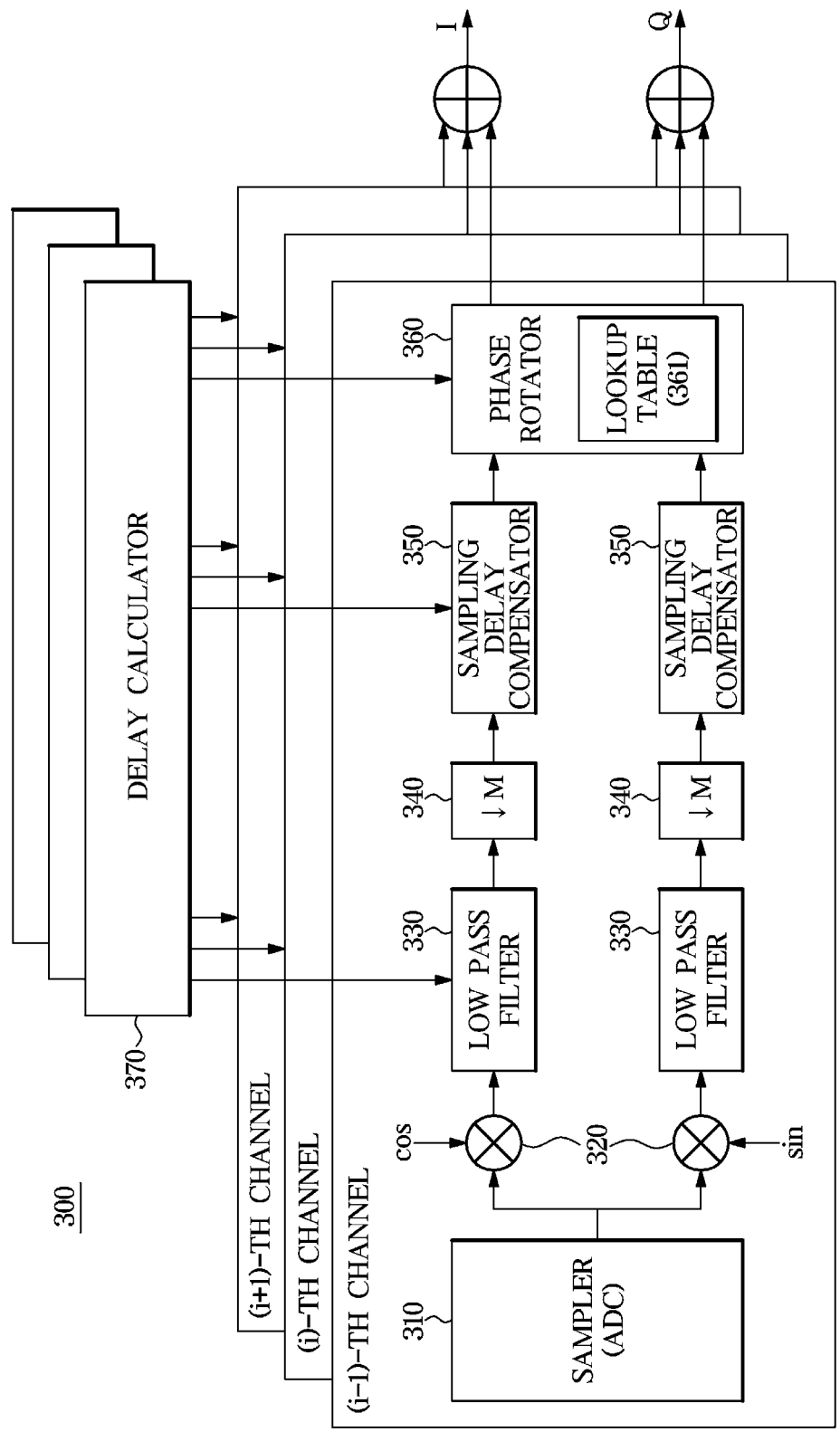
FIG. 5 is a control block diagram specifically illustrating a beamformer according to an embodiment.

FIG. 5 is a control block diagram specifically illustrating a beamformer according to an embodiment.

Referring to FIG. 5, the beamformer 300 corresponds to the digital beamformer, and may include a sampler 310, a mixer 320, a low pass filter 330, a decimator 340, a sampling delay compensator 350, a phase rotator 360, and a delay calculator 370.

The sampler 310 may perform sampling to convert the analog signal received through each channel into the digital signal.

When the ultrasound signal beamforming, in order to obtain a high-resolution ultrasound image, the time delay value normally allocated to each transducer element should be sampled at 16 times a center frequency $f_0$ of the transducer element, but after sampling at a relatively low frequency in consideration of the ADC performance and required memory size, a method of interpolating the time delay value is used in the low pass filter 330. For example, the signal is sampled at a sampling frequency corresponding to 4 times the center frequency, and then a resolution corresponding to 16 times the center frequency may be obtained through 4 times interpolation.

The mixer 320 may perform COS and SIN multiplication based on the center frequency on the sampled signal to separate the sampled signal into an in-phase component signal and a quadrature component signal.

The low pass filter 330 may interpolate the sampled signal. The low pass filter 330 may interpolate the sampled signal based on the time delay resolution received from the delay calculator 370 including an interpolation filter. The time delay resolution may refer to a value corresponding to an interpolation factor of the sampling frequency. That is, the time delay error due to sampling may be reduced by increasing a sampling rate by the time delay resolution (interpolation factor). A process of inducing a sampling time delay and an interpolation process are further described below with reference to FIGS. 8 and 9.

In addition, the low pass filter 330 may perform filtering for removing signals other than the baseband on the in-phase component signal and the quadrature component signal.

That is, the sampled signal may be separated into the in-phase component signal and the quadrature component signal through a quadrature demodulation process though cos(w0nT), −sin(w0nT) multiplication, and the low pass filter 330, and may be moved to the baseband.

The decimator 340 may perform decimation on the filtered in-phase component signal and quadrature component signal. The decimation may refer to reducing an amount of data that has been increased through the interpolation by a certain percentage. The decimator 340 may reduce the amount of data by a specific ratio in a range where there is no aliasing error.

The sampling delay compensator 350 may compensate the sampling time delay for the decimated in-phase component signal and the quadrature component signal based on a preset time delay resolution. The sampling time delay may refer to the time delay generated by sampling a total time required for the ultrasound echo signal reflected from the image point to reach the transducer element after the ultrasound signal is transmitted to the image point, as the sampling frequency. The sampling delay compensator 350 may compensate for a fine time delay with respect to an amplitude based on the time delay resolution input from the delay calculator 370 for the signal interpolated by the low pass filter 330.

The phase rotator 360 may compensate for the in-phase component signal and the quadrature component signal for which the sampling time delay is compensated, based on a preset phase resolution. The phase resolution may refer to a value corresponding to the phase quantization level. In the disclosure, the time delay resolution and the phase resolution are independently applied and may have different values.

Figure 6:
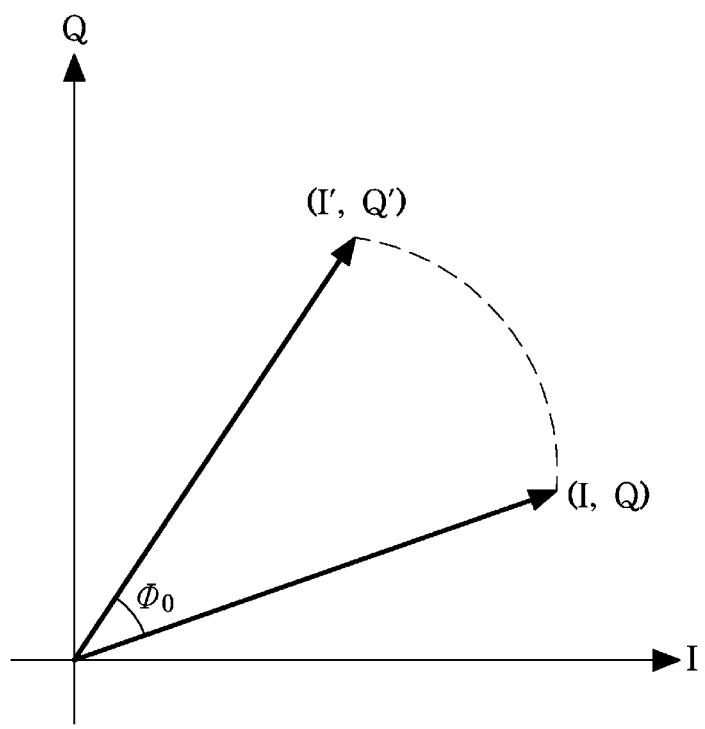
FIG. 6 is a view for describing phase rotation in a complex plane.
Figure 7:
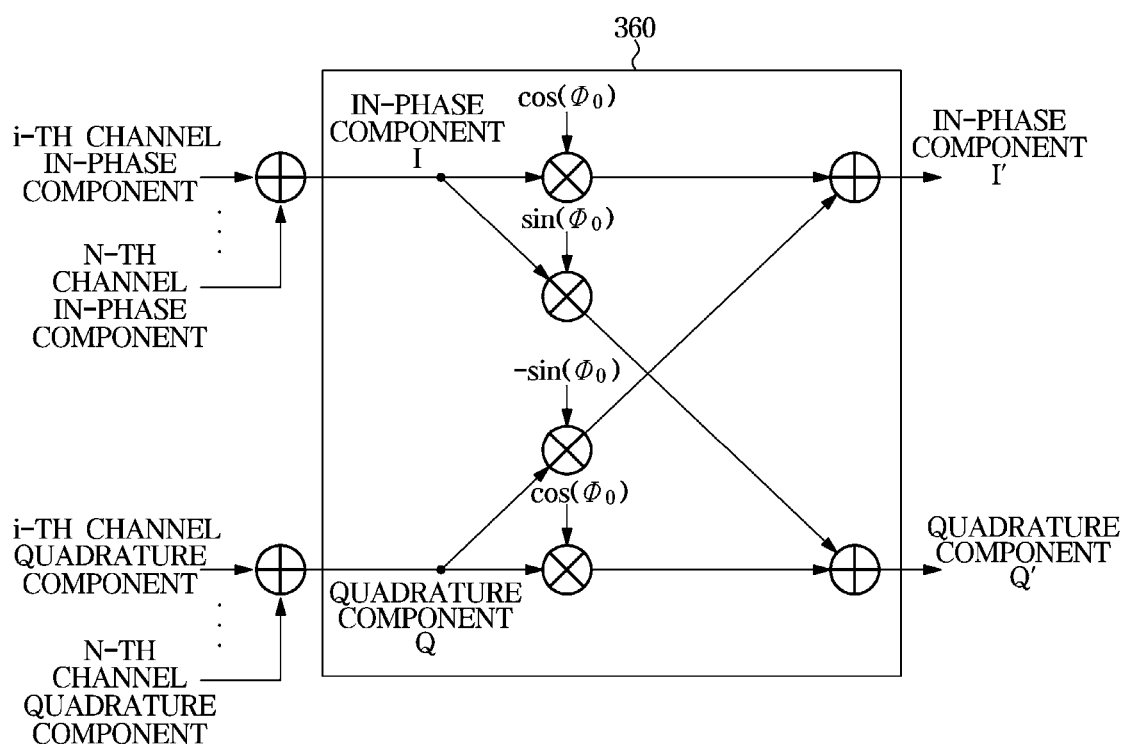
FIG. 7 is a view illustrating an internal structure of a phase rotator.

FIG. 6 is a view for describing phase rotation in a complex plane, and FIG. 7 is a view illustrating an internal structure of a phase rotator.

Referring to FIGS. 6 and 7, a phase rotation process in a complex plane may be described through Equation 1 below.

$$(I+jQ)e^{j(\phi_0 \Delta \tau)} = (I+jQ) \cdot (\cos(\phi_0)+j \sin(\phi_0))$$

$$= [I \cdot \cos(\phi_0) - Q \cdot \sin(\phi_0)] + j[Q \cdot \cos(\phi_0) + I \cdot \sin(\phi_0)]$$

$$I'+jQ'$$

$$I \cdot \cos(\phi_0) - Q \cdot \sin(\phi_0)$$

$$Q' = Q \cdot \cos(\phi_0) + I \cdot \sin(\phi_0) \quad \text{[Equation 1]}$$

Meanwhile, the phase rotator 360 may include a lookup table 361 storing a phase delay compensation value corresponding to the phase resolution. The phase rotator 360 may compensate for the phase delay based on the phase delay compensation value stored in the lookup table 361. Particularly, the phase rotator 360 may calculate the phase delay compensation value using a preset relationship and the phase resolution of a distance from the focal point to the element of the transducer array and store the calculated phase delay compensation value in the lookup table 361.

At this time, an address of the lookup table 361 in which the phase delay compensation value is stored may also be calculated using the preset relationship and the phase resolution between the distance from the focal point to the element of the transducer array and the ultrasound wavelength.

The preset relationship between the distance from the focal point to the element of the transducer array and the ultrasound wavelength may be a relationship defined as a value obtained by dividing the distance from the focal point to a center element of the transducer array and any other element by the ultrasound wavelength. A process of calculating the phase delay compensation value and the address of the lookup table 361 will be described in detail with reference to FIGS. 11 and 12 below.

Referring back to FIG. 5, the delay calculator 370 may independently calculate the time delay resolution and the phase resolution and apply them to the low pass filter 330, the sampling delay compensator 350, and the phase rotator 360, respectively. Particularly, the delay calculator 370 may calculate the time delay resolution and the phase resolution as different values using an error model defined based on an average of the amplitude error and an average of the phase error. The time delay resolution and the phase resolution may be input from the user through the input 540 of the ultrasound diagnostic apparatus 1.

The amplitude error may refer to an error in a size error of the ultrasound signal caused by an error between the sampled time delay and the time delay of the original signal according to the time delay resolution, and the phase error may refer to an error between the quantized phase and the phase delay of the original signal according to the phase resolution. The error model refers to an average of baseband ultrasound signal errors derived based on the average of the amplitude errors and the average of the phase errors. The error model may be described together in FIG. 10.

In this way, since the disclosure can set the phase resolution to a value different from the time delay resolution, it is possible to increase the resolution of the ultrasound image by setting only the phase resolution to be high without the need to increase an interpolator required to increase the time delay resolution. That is, since the beamforming performance can be improved only by increasing a memory size of the lookup table 361 required to increase the phase resolution, the hardware complexity may be reduced, and heat generation and power consumption may be reduced.

Figure 8:
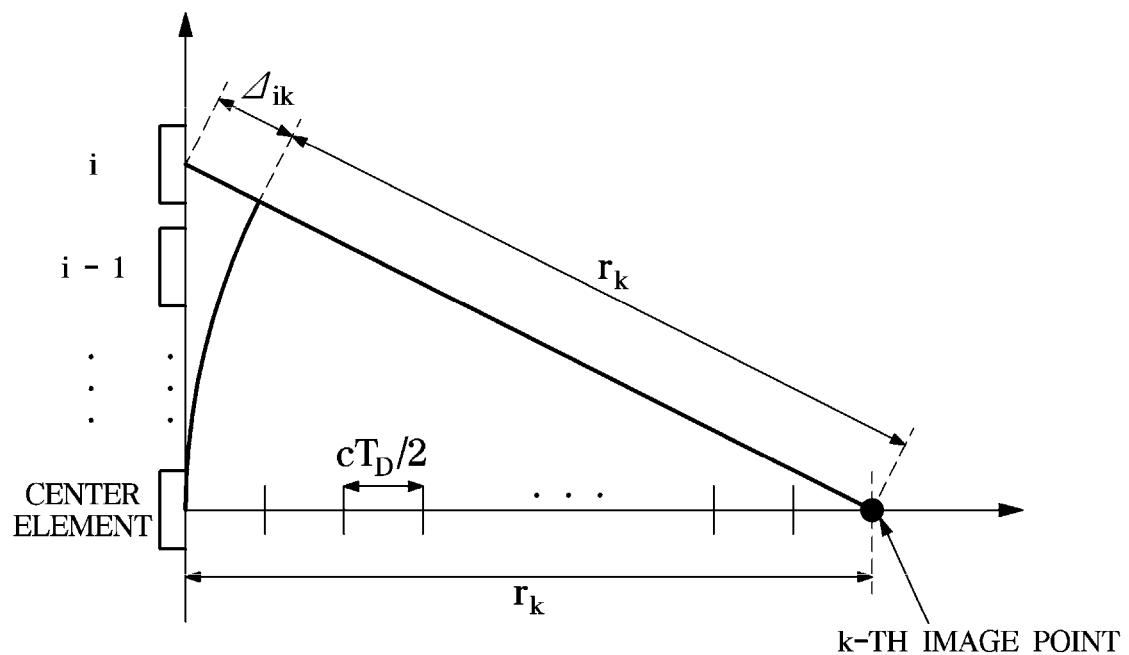
FIG. 8 is a view illustrating a model of a transmission/reception distance of an ultrasound signal.
Figure 9:
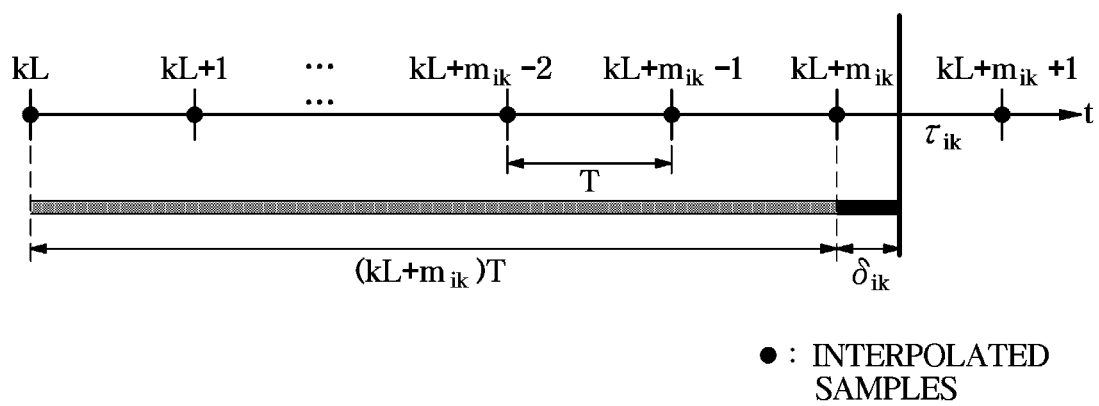
FIG. 9 is a view for describing sampling of a time delay.

FIG. 8 is a view illustrating a model of a transmission/reception distance of an ultrasound signal, and FIG. 9 is a view for describing sampling of a time delay.

Referring to FIG. 8, first, the ultrasound signal may be defined as in Equation 2 below.

$$f(t)=\alpha(t)\cos(\omega_0 t) \quad \text{[Equation 2]}$$

In FIG. 8, after transmitting the ultrasound signal based on the center element, the ultrasound signal received by an i-th element by reflecting the ultrasound at an arbitrary image point may be defined as in Equation 3 below.

$$x_i(t)=\alpha(t-\tau_i(r_k))\cos(\omega_0(t-\tau_i(r_k))) \quad \text{[Equation 3]}$$

At this time, $\tau_i(r)$ may refer to the total time taken for the ultrasound signal to be reflected from the image point at a distance of $r_k$ and received by the i-th element, and may be expressed as Equation 4 below.

$$\tau_i(r_k) = \frac{r_k + r_{ik}}{C}, \quad r_{ik} = r_k + \Delta_{ik} \quad \text{[Equation 4]}$$

c may represent a progression speed (average 1540 m/s) of the ultrasound signal transmitted into a human tissue.

When the distance to the image point is represented by a sampling period $cT_D/2$, the distance $r_k$ from the k-th image point to the center element and a distance $r_{ik}$ from the i-th element are as in Equation 5 below.

$$r_k = k \cdot \frac{cT_D}{2} = k \cdot \frac{cLT}{2}, \quad r_{ik} = k \cdot \frac{cLT}{2} + \Delta_{ik} \quad \text{[Equation 5]}$$

Figure 10:
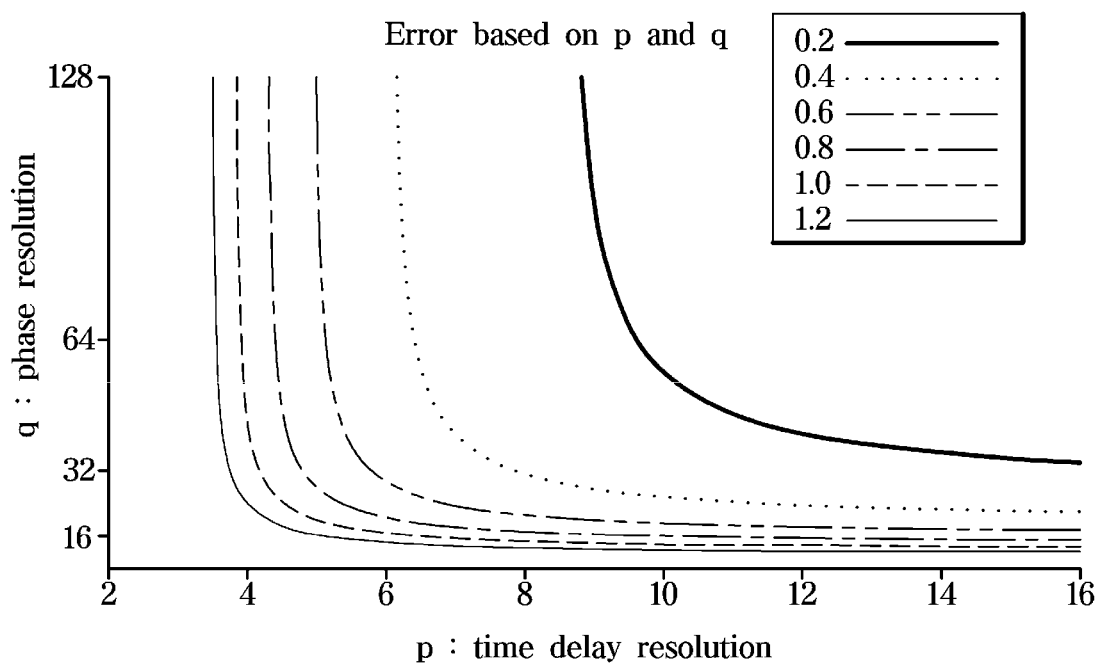
FIG. 10 is a graph illustrating an average error according to a time delay resolution and a phase resolution.

T is a sampling period ($T=T_D/L$) obtained by interpolating the sampling period by L times. The interpolation factor L may be defined as the time delay resolution. In FIG. 10, the time delay resolution may be denoted by p.

$\Delta_{ik}$ may refer to a sum of a residual distance (mik*T*c) corresponding to the sampling period and the residual distance (δik*c) corresponding to the fine delay time period.

Therefore, the sampled total delay time $\tau_{ik}(r_k)$ may be expressed as Equation 6 below.

$$\tau_{ik}(r_k) = \frac{r_k + r_{ik}}{c} = (kL + m_{ik})T + \delta_{ik} \quad \text{[Equation 6]}$$

(k, L, $m_{ik}$ are integers)

FIG. 9 illustrates that the time delay is sampled with the sampling period interpolated by L times.

In addition, an ultrasound received signal reflecting $\tau\_ik$ (r_k) may be written as in Equation 7 below.

$$x_{ik}(t)=\alpha(t-kLT-m_{ik}T-\delta_{ik})\cos(\omega_0(t-kLT-m_{ik}T-\delta_{ik})) \quad \text{[Equation 7]}$$

The sampled ultrasound received signal may be separated into the in-phase component signal and the quadrature component signal. In other words, in-phase data and quadrature data may be generated through quadrature demodulation through the low pass filter by multiplying the sampled ultrasound received signal by cos and −sin, respectively.

When the in-phase signal $i_i(nT)$ and the quadrature signal $q_i(nT)$ are expressed as a time index (nT), it is as illustrated in Equation 8 below.

$$i_i(nT)=x_{ik}(nT)\cos(\omega_0 nT)|_{LPF}=a(nT-\tau_{ik}(r_k))\cos(\omega_0\tau_{ik}(r_k))$$

$$q_i(nT)=-x_{ik}(nT)\sin(\omega_0 nT)|_{LPF}=-a(nT-\tau_{ik}(r_k))\sin(\omega_0\tau_{ik}(r_k)) \quad \text{[Equation 8]}$$

When the in-phase component signal and the quadrature component signal are expressed as an analytic signal, it is as illustrated in Equation 9 below, and this is referred to as a baseband signal.

$$z_i(nT)=i_i(nT)+jq_i(nT)=\alpha(nT-\tau_{ik})\exp(j\omega_0\tau_{ik}) \quad \text{[Equation 9]}$$

Here, in order to restore an ultrasound signal a(0) reflected from the image point, the time delay $\tau_{ik}$ and a phase delay $\exp(j\omega_0\tau_{ik})$ must be compensated. The time delay may be compensated by taking a sample (n) corresponding to a natural number closest to $\tau_{ik}/T$, and the phase delay may be compensated by multiplying the sample by the quantized phase value closest to $\exp(-j\omega_0\tau_{ik})$.

However, since both the time delay and the phase delay are compensated by the sampled value, the amplitude error and the phase error according to the sampling error occur. The amplitude error may be compensated by increasing the time delay resolution, and the phase error may be compensated by increasing the phase resolution. However, since the interpolator must be added to increase the time delay resolution, there is a problem in that hardware complexity is greatly increased compared to the phase resolution improvement that can be solved by increasing a memory size.

Accordingly, the disclosure aims to improve the beamforming performance and reduce the hardware complexity by independently setting the time delay resolution and the phase resolution and setting the phase resolution higher than the time delay resolution.

FIG. 10 is a graph illustrating an average error according to a time delay resolution and a phase resolution.

A graph shown in FIG. 10 represents an error average of the baseband signal derived based on the average of the amplitude error and atheaverage of a phase error. In the disclosure, the error average of the baseband signal is defined as the error model, and an optimal time delay resolution and phase resolution that can improve the beamforming performance without causing the hardware complexity may be calculated using the error model.

Particularly, in FIG. 10, it can be seen that the error of the baseband signal is equal to 0.8 when a time delay resolution p is 16 and a phase resolution q is 16 and the time delay resolution p is 4.7 and the phase resolution q is 64. Therefore, when the time delay resolution is reduced to 5 and the phase resolution is set to 6, the same performance may be obtained simply by increasing the memory size of the lookup table 361 by 2 bits while reducing the number of interpolators. In this case, compared to the time delay resolution of 16, the hardware complexity is reduced, and heat generation and power consumption may be reduced.

A process of deriving the error model is as follows.

First, if the time index nT of the sampled baseband signal illustrated in Equation 9 is expressed as $\tau_{ik}'$ and $\omega\_0\tau\_ik$ is expressed as $\Phi$, the baseband signal $S_{iq}$ and the time delay error $\delta_t$ may be written as in Equation 10 below.

$$s_{iq}=a(\tau_{ik}'-\tau_{ik})\exp(j\Phi), \Phi=\omega_0\tau_{ik}$$

$$\delta_t=\tau_{ik}'-\tau_{ik}(-T/2\leq\delta_t<T/2) \quad \text{[Equation 10]}$$

In Equation 10 above, $\exp(j\Phi)$ is a phase component of the baseband signal, so it is independent of time. Therefore, when the phase component is compensated by multiplying the quantized $\exp(-j\Phi_q)$ by the phase resolution q, the baseband signal compensated for the phase delay and the phase error $\delta_p$ are as illustrated in Equation 11 below.

$$s_{iq}=a(\tau_{ik}'-\tau_{ik})\exp(j(\Phi-\Phi_q))$$

$$\delta_p=\Phi-\Phi_q(-\pi/q\leq\delta_p<\pi/q) \quad \text{[Equation 11]}$$

When there are no time delay error $\delta_t$ and phase error $\delta_p$, the value of the baseband signal is a(0)=1. The time delay error and the phase error act independently, and the amplitude a(t) of the baseband signal represents a shape of the Gaussian function. Assuming that the time delay error $\delta_t$ and the phase error $\delta_p$ each have a uniform distribution, an error $\varepsilon_{IQ}$ of the baseband signal is illustrated in Equation 12 below.

$$\varepsilon_{IQ} = 1 - a(\delta_t)\exp(j\delta_p)a(\delta_t) = \exp\left(-\frac{\delta_t^2}{t_0^2}\right) \quad \text{[Equation 12]}$$

In addition, an average of the amplitude error $\text{avg}(\varepsilon_{env})$, an average of the phase error $\text{avg}(\varepsilon_p)$, and an average of the baseband signal error $\text{avg}(\varepsilon_{IQ})$ may be expressed as Equation 13 below.

$$\text{avg}(\varepsilon_{env}) = \quad \text{[Equation 13]}$$

$$E[\varepsilon_{env}(t)] = 1 - \sqrt{\pi}t_0\exp(-\pi^2f^2t_0^2)*\text{sinc}(fT)|_{f=0}$$

$$\text{avg}(\varepsilon_p) = 1 - \text{sinc}\left(\frac{1}{q}\right)$$

$$\text{avg}(\varepsilon_{IQ}) = 1 - (1 - \text{avg}(\varepsilon_{env}))\cdot(1 - \text{avg}(\varepsilon_p))$$

Figure 11:
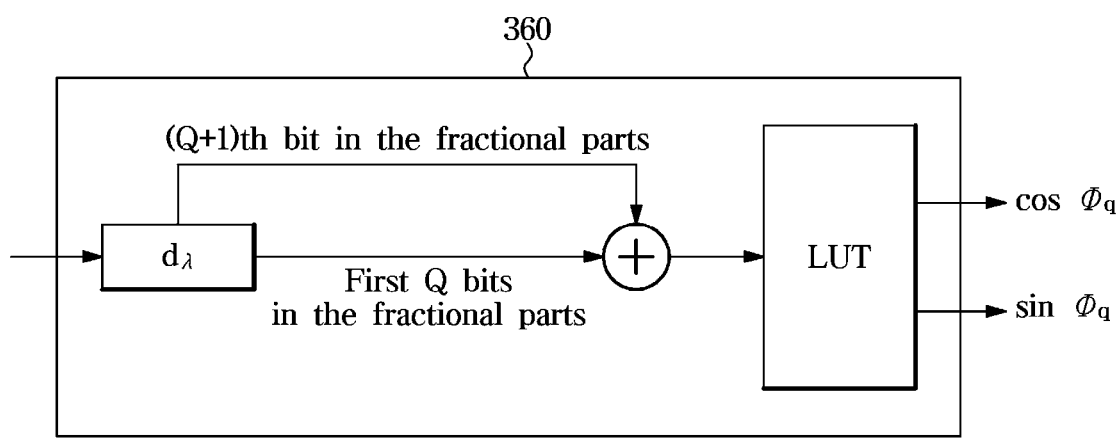

FIGS. 11 and 12 are views for describing a method of configuring a lookup table.

A method of calculating the address of the lookup table 361 in which the phase delay compensation value and the phase delay compensation value are stored will be described with reference to FIGS. 11 and 12.

Assuming that the phase resolution, which is the phase quantization level, is M, and the number of bits required for addressing the lookup table 361 is Q bits, M and Q have an M=2^Q relationship. For example, when the phase resolution M is 64, the required number of memory bits of the lookup table 361 is 6 bits.

The address of the lookup table 361 storing the phase delay compensation value and the phase delay compensation value is the distance $r_k$ from the k-th image point to the center element and the distance rik from the i-th element shown in FIG. 8 as the wavelength of the ultrasound wave.

It can be calculated using the divided value dλ. That is, $d_{80}$ is equal to Equation 14 below.

$$d_{80} =(r_k+r_{ik})/\lambda=d_{ik}/\lambda \quad \text{[Equation 14]}$$

For phase delay compensation, $\exp(-j\omega_0\tau_{ik})$ to be multiplied by the baseband signal of Equation 9 is again expressed using da, as Equation 15 below.

$$\exp\left(-j\omega_0\frac{d_{ik}}{c}\right) = \exp(-j2\pi d_\lambda) = \exp(-j2\pi\cdot(\lfloor d_\lambda\rfloor + frac(d_\lambda))) \quad \text{[Equation 15]}$$

$$= \exp(j2\pi\cdot frac(d_\lambda))$$

Here, frac(dλ) is a decimal value of dλ and [dλ] is an integer value, so $\exp(j2\pi\cdot(\lfloor d\lambda\rfloor))=1$, leaving only the decimal term. Therefore, the phase rotation may be performed by referring only to the prime value of dλ.

When the phase resolution is M, the quantized phase $\Phi_q$ may be summarized as in Equation 16 below.

$$\phi_q = 2\pi\cdot\frac{1}{M}\lfloor M\cdot frac(d_\lambda) + 0.5\rfloor = 2\pi\cdot\frac{m}{M} \quad m = 0, 1, \quad \text{[Equation 16]}$$

$$\ldots, M-1$$

As illustrated in FIG. 11, the address of the lookup table 361 may be calculated by adding the Q+1 th bit in the fractional part of $d_\lambda$ with the Q bit. n the calculated address of the lookup table 361, $\cos(\Phi_q)$, $\sin(\Phi_q)$ values are stored as illustrated in FIG. 12.

In this way, the disclosure does not calculate an ideal phase value for the phase delay compensation, but performs the phase rotation using the quantized phase value stored in the lookup table 361, thereby simplifying the operation process and reducing the hardware complexity.

FIG. 13 is a view for comparing a beamforming image output according to a prior art and the disclosure.

Figure 13B:
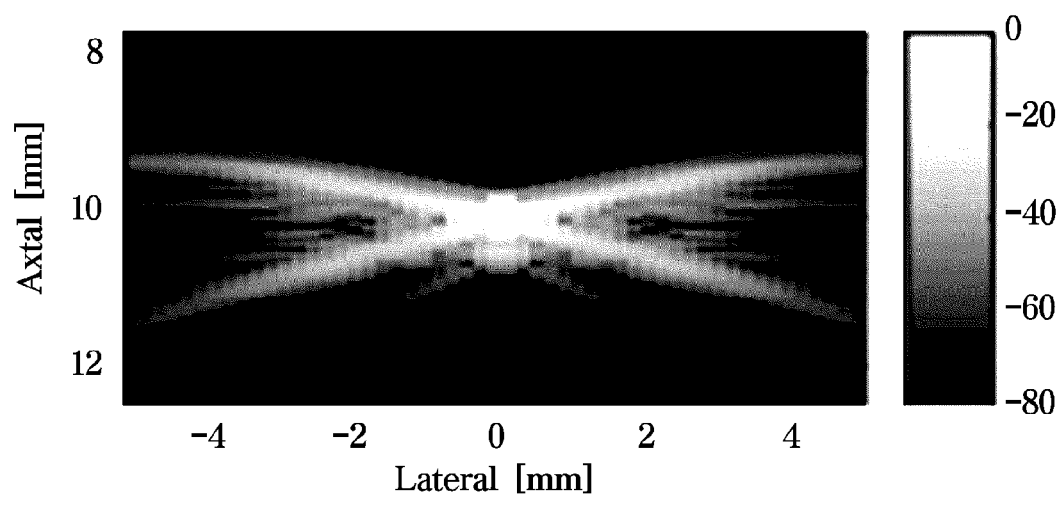
FIG. 13 is a view for comparing a beamforming image output according to a prior art and the disclosure.

FIG. 13A is a beamforming image output according to the prior art, and FIG. 13B is a beamforming image output according to the disclosure.

The prior art may output a point spread function as illustrated in FIG. 13A by applying the time delay resolution and the phase resolution to the same level of 16. On the other hand, the disclosure may independently set the phase resolution, and output an image as illustrated in FIG. 13B by setting the resolution higher than the time delay resolution. That is, it can be seen that the disclosure can obtain the image with a small side lobe by setting the phase resolution high.

FIG. 14 is a flowchart of a beamforming method according to an embodiment.

First, as described in FIG. 5, the beamformer 300 included in the beamforming device 100 may include the sampler 310, the mixer 320, the low pass filter 330, the decimator 340, and the sampling delay compensator 350, the phase rotator 360, and the delay calculator 370.

Referring to FIG. 14, the beamforming device 100 samples the ultrasound signal reflected from the focal point and received by the transducer array (S901). The beamforming device 100 separates the sampled signal into the in-phase component signal and the quadrature component signal (S902). The beamforming device 100 calculates the time delay resolution and the phase resolution, respectively (S903), and performs filtering for the in-phase component signal and the quadrature component signal in a preset band to move the ultrasound signal to the baseband (S904). The beamforming device 100 performs decimation on the filtered in-phase component signal and quadrature component signal (S905). In addition, the beamforming device 100 compensates for the sampling time delay based on the time delay resolution for the decimated in-phase component signal and the quadrature component signal (S906). Thereafter, for the in-phase component signal and the quadrature component signal for which the sampling time delay is compensated, the phase delay is compensated based on the phase resolution (S907).

As described above, since the disclosure can set the phase resolution to the value different from the time delay resolution, it is possible to increase the resolution of the ultrasound image by setting only the phase resolution to be high without the need to increase the interpolator required to increase the time delay resolution. That is, since the beamforming performance can be improved only by increasing the memory size of the lookup table 361 required to increase the phase resolution, the hardware complexity may be reduced, and heat generation and power consumption may be reduced.

In addition, the disclosure may simplify the calculation process by performing the phase rotation using the quantized phase value stored in the lookup table 361 without calculating the ideal phase value for the phase delay compensation.

The disclosed embodiments may be implemented in the form of a recording medium storing computer-executable instructions that are executable by a processor. The instructions may be stored in the form of a program code, and when executed by a processor, the instructions may generate a program module to perform operations of the disclosed embodiments. The recording medium may be implemented non-transitory as a computer-readable recording medium.

The non-transitory computer-readable recording medium may include all kinds of recording media storing commands that can be interpreted by a computer. For example, the non-transitory computer-readable recording medium may be, for example, ROM, RAM, a magnetic tape, a magnetic disc, flash memory, an optical data storage device, etc.

Embodiments of the disclosure have thus far been described with reference to the accompanying drawings. It should be obvious to a person of ordinary skill in the art that the disclosure may be practiced in other forms than the embodiments as described above without changing the technical idea or essential features of the disclosure. The above embodiments are only by way of example, and should not be interpreted in a limited sense.

The invention claimed is:

1. A beamforming device comprising:
a sampler configured to sample a signal reflected from a focal point and received to a transducer array;
a mixer configured to separate the sampled signal into an in-phase component signal and a quadrature component signal;
a low pass filter configured to perform filtering on the in-phase component signal and the quadrature component signal;
a decimator configured to perform decimation on the filtered in-phase component signal and quadrature component signal;
a sampling delay compensator configured to compensate a sampling time delay based on a preset time delay resolution for the decimated in-phase component signal and quadrature component signal;
a phase rotator configured to compensate a phase delay based on a preset phase resolution for the in-phase component signal and the quadrature component signal for which the sampling time delay is compensated; and
a delay calculator configured to calculate a time delay resolution and the phase resolution, and to apply each to the sampling delay compensator and the phase rotator,
wherein the delay calculator is configured to calculate the time delay resolution and the phase resolution as different values using an error model defined based on an average of an amplitude error and an average of a phase error.

2. The beamforming device according to claim 1, wherein the phase rotator comprises a look up table configured to store a phase delay compensation value corresponding to the phase resolution, and is configured to compensate the phase delay by referring to the lookup table.

3. The beamforming device according to claim 1, wherein the low pass filter comprises an interpolation filter configured to increase an amount of data of the in-phase component signal and the quadrature component signal according to the time delay resolution.

4. The beamforming device according to claim 2, wherein the phase rotator is configured to:
calculate the phase delay compensation value using a preset relationship between a distance from the focal point to an element of the transducer array and an ultrasound wavelength and the phase resolution; and
store the calculated phase delay compensation value in the lookup table.

5. The beamforming device according to claim 2, wherein the phase rotator is configured to calculate an address of the lookup table to be referred using a preset relationship between a distance from the focal point to an element of the transducer array and an ultrasound wavelength and the phase resolution.

6. A method of controlling a beamforming device comprising:
sampling, by a sampler, a signal reflected from a focal point and received to a transducer array;
separating, by a mixer, the sampled signal into an in-phase component signal and a quadrature component signal;
calculating, by a delay calculator, a time delay resolution and a phase resolution as different values using an error model defined based on an average of an amplitude error and an average of a phase error;
filtering, by a low pass filter, the in-phase component signal and the quadrature component signal in a preset band;
performing, by a decimator, decimation on the filtered in-phase component signal and quadrature component signal;
compensating, by a sampling delay compensator, a sampling time delay based on the time delay resolution for the decimated in-phase component signal and quadrature component signal; and
compensating, by a phase rotator, a phase delay based on the phase resolution for the in-phase component signal and the quadrature component signal for which the sampling time delay is compensated.

7. The method according to claim 6, wherein the compensating of the phase delay comprises:
compensating the phase delay by referring to a look up table stored a phase delay compensation value corresponding to the phase resolution.

8. The method according to claim 6, wherein the filtering further comprises:
   performing an interpolation to increase an amount of data of the in-phase component signal and the quadrature component signal according to the time delay resolution.

9. The method according to claim 7, wherein the compensating of the phase delay further comprises:
   calculating the phase delay compensation value using a preset relationship between a distance from the focal point to an element of the transducer array and an ultrasound wavelength and the phase resolution; and
   storing the calculated phase delay compensation value in the lookup table.

10. The method according to claim 7, wherein the compensating of the phase delay further comprises:
    calculating an address of the lookup table to be referred using a preset relationship between a distance from the focal point to an element of the transducer array and an ultrasound wavelength and the phase resolution.

11. An ultrasound diagnostic apparatus comprising:
    a probe including a transducer array configured to transmit and receive ultrasound signals, and a beamforming device; and
    a main body configured to process the signal received from the probe to generate an ultrasound image, and to display the generated ultrasound image,
    wherein the beamforming device comprises:
      a sampler configured to sample the signal reflected from a focal point and received to the transducer array;
      a mixer configured to separate the sampled signal into an in-phase component signal and a quadrature component signal;
      a low pass filter configured to perform filtering on the in-phase component signal and the quadrature component signal;
      a decimator configured to perform decimation on the filtered in-phase component signal and quadrature component signal;
      a delay calculator configured to calculate a time delay resolution and a phase resolution as different values using an error model defined based on an average of an amplitude error and an average of a phase error;
      a sampling delay compensator configured to configured to compensate a sampling time delay based on the delay resolution for the decimated in-phase component signal and quadrature component signal; and
      a phase rotator configured to compensate a phase delay based on the phase resolution for the in-phase component signal and the quadrature component signal for which the sampling time delay is compensated.

12. The ultrasound diagnostic apparatus according to claim 11, wherein the phase rotator comprises a look up table configured to store a phase delay compensation value corresponding to the phase resolution, and is configured to compensate the phase delay by referring to the lookup table.

13. The ultrasound diagnostic apparatus according to claim 12, wherein the phase rotator is configured to:
    calculate the phase delay compensation value using a preset relationship between a distance from the focal point to an element of the transducer array and an ultrasound wavelength and the phase resolution; and
    store the calculated phase delay compensation value in the lookup table.

14. The ultrasound diagnostic apparatus according to claim 12, wherein the phase rotator is configured to calculate an address of the lookup table to be referred using a preset relationship between a distance from the focal point to an element of the transducer array and an ultrasound wavelength and the phase resolution.

* * * * *